(12) United States Patent
Lee

(10) Patent No.: US 9,968,736 B2
(45) Date of Patent: May 15, 2018

(54) LIQUID INJECTOR FOR CONTINUOUSLY INJECTING FIXED QUANTITY OF CHARGED LIQUID

(71) Applicant: ACE MEDICAL CO., LTD., Goyang-si, Gyeonggi-do (KR)

(72) Inventor: Jong-Woo Lee, Seoul (KR)

(73) Assignee: Ace Medical Co., Ltd., Goyang-si (KR)

( * ) Notice: Subject to any disclaimer, the term of this patent is extended or adjusted under 35 U.S.C. 154(b) by 0 days. days.

(21) Appl. No.: 14/961,041

(22) Filed: Dec. 7, 2015

(65) Prior Publication Data

US 2017/0106137 A1  Apr. 20, 2017

(30) Foreign Application Priority Data

Oct. 20, 2015 (KR) ........................ 10-2015-0145929

(51) Int. Cl.
*A61M 5/145* (2006.01)
*A61M 5/152* (2006.01)
*A61M 5/162* (2006.01)
*A61M 5/30* (2006.01)
*A61M 5/14* (2006.01)

(52) U.S. Cl.
CPC .......... *A61M 5/1452* (2013.01); *A61M 5/152* (2013.01); *A61M 5/162* (2013.01); *A61M 5/30* (2013.01); *A61M 2005/1402* (2013.01); *A61M 2005/1405* (2013.01)

(58) Field of Classification Search
CPC ........ A61M 2005/1405; A61M 5/1452; A61M 5/152; A61M 5/162; A61M 5/30; A61M 2005/1402
See application file for complete search history.

(56) References Cited

U.S. PATENT DOCUMENTS

| | | | |
|---|---|---|---|
| 6,206,850 B1 * | 3/2001 | O'Neil ................ | A61M 5/1424 604/132 |
| 8,211,089 B2 * | 7/2012 | Winsor ............... | A61M 39/045 604/284 |
| 2004/0127860 A1 * | 7/2004 | Rake ................. | A61M 5/14216 604/246 |

* cited by examiner

*Primary Examiner* — Nathan R Price
*Assistant Examiner* — John Doubrava
(74) *Attorney, Agent, or Firm* — Jefferson IP Law, LLP

(57) ABSTRACT

A liquid injector that additionally supplies charged liquid to a patient is provided. The liquid injector continuously supplies a fixed quantity of liquid to a patient only when the fixed quantity of liquid has been charged.

6 Claims, 10 Drawing Sheets

LIQUID INJECTOR FOR CONTINUOUSLY INJECTING FIXED QUANTITY OF CHARGED LIQUID

CROSS-REFERENCE TO RELATED APPLICATION(S)

This application claims the benefit under 35 U.S.C. § 119(a) of a Korean patent application filed on Oct. 20, 2015 in the Korean Intellectual Property Office and assigned Serial number 10-2015-0145929, the entire disclosure of which is hereby incorporated by reference.

TECHNICAL FIELD

The present disclosure relates to a liquid injector that additionally supplies charged liquid to a patient. More particularly, the present disclosure relates to a liquid injector that continuously supplies a fixed quantity of liquid to a patient only when the fixed quantity of liquid has been charged.

BACKGROUND

In general, if a patient has a surgical operation, he or she feels a pain around where he or she has had the surgery. Then, the degrees of pain felt by the patients are different according to the kinds of the surgical operations and operation spots, and in particular, the degrees of pain felt by the patients are different, depending on the individual characteristics of the patients even though the same kind of surgical operations are conducted.

Accordingly, together with a liquid injector (KR 10-0519247 B1) that continuously injects an analgesic to alleviate the pain of the patient, a liquid injector patient controlled analgesia (PCA) that can additionally inject an analgesic when the patient complains of pain are necessary. That is, a liquid injector is installed between a liquid supply and a catheter according to the related art, and catches and charges the liquid at an intermediate point when the liquid supply continuously sends the liquid to the catheter and additionally sends the liquid whenever it is necessary to alleviate the pain of the patient.

However, the catheter connected to the liquid injector is inserted into a vein or an epidural space of a patient to inject liquid into the body of the patient, and the catheter generally has a diameter of about 2 mm and is thin and long and thus the quantity of injected liquid is small and the injection speed of the liquid is also low.

Accordingly, the recharging time of the liquid injector for catching and charging the liquid at an intermediate point is long because the injection speed of the liquid is low, and in particular, even when the charged liquid is to be additionally introduced by pushing the button of the liquid injector, the quantity of the introduced liquid is not constant so that it is difficult to identify how much the liquid has been injected into the body of the patient.

That is, as the liquid is repeatedly injected into the body of the patient while the liquid is not completely charged, it is not identified how much the liquid corresponding to a narcotic analgesic is injected into the body of the patient.

The above information is presented as background information only to assist with an understanding of the present disclosure. No determination has been made, and no assertion is made, as to whether any of the above might be applicable as prior art with regard to the present disclosure.

SUMMARY

Aspects of the present disclosure are to address at least the above-mentioned problems and/or disadvantages and to provide at least the advantages described below. Accordingly, an aspect of the present disclosure is to provide a liquid injector that can inject a fixed quantity of liquid into the body of a patient while automatically charging the liquid and can continuously supply the fixed quantity of liquid into the body of the patient so that the liquid injector can be safely used.

In accordance with an aspect of the present disclosure, a liquid injector that additionally supplies charged liquid while continuously injecting a small quantity of liquid is provided. The liquid injector includes a fixed quantity charging unit that is adhered to a lower end of a push button when a piston is lifted by liquid introduced into the interior of a cylinder and then is stopped to charge a fixed quantity of liquid in the interior of the cylinder, a brake button unit that, if the lifted piston and the push button are adhered to each other while the downward movement of the push button is stopped, lowers the push button together with the piston downwards as the stopped downward movement of the push button is released, and a continuous injection unit that, by a restoring force of a resilient tube that is expanded while accommodating a fixed quantity of liquid discharged to the outside of the cylinder by the brake button unit, continuously pushes out the liquid accommodated in the interior of the resilient tube.

The liquid injector according to the present disclosure can charge a fixed quantity of liquid while automatically charging the liquid, and can continuously inject the liquid into the body of the patient little by little while absorbing the fixed quantity of discharged liquid so that the liquid injector can be safely used.

Other aspects, advantages, and salient features of the disclosure will become apparent to those skilled in the art from the following detailed description, which, taken in conjunction with the annexed drawings, discloses various embodiments of the present disclosure.

BRIEF DESCRIPTION OF THE DRAWINGS

The above and other aspects, features, and advantages of certain embodiments of the present disclosure will be more apparent from the following description taken in conjunction with the accompanying drawings, in which.

Throughout the drawings, it should be noted that like reference numbers are used to depict the same or similar elements, features, and structures.

DETAILED DESCRIPTION

The following description with reference to the accompanying drawings is provided to assist in a comprehensive understanding of various embodiments of the present disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the present disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

Figure 1:
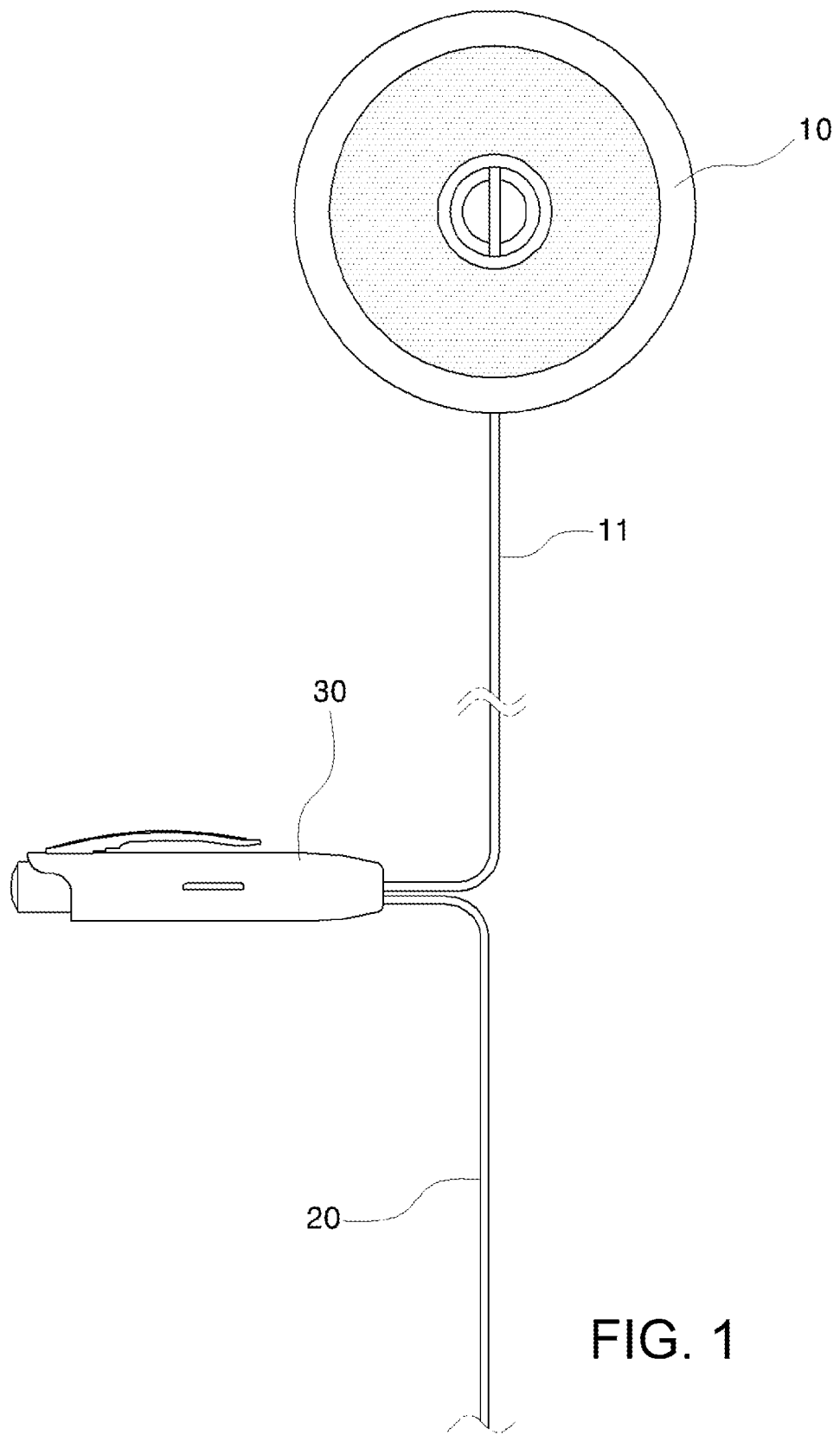
FIG. 1 is a view illustrating an in-use state of a liquid injector according to an embodiment of the present disclosure.
Figure 2:
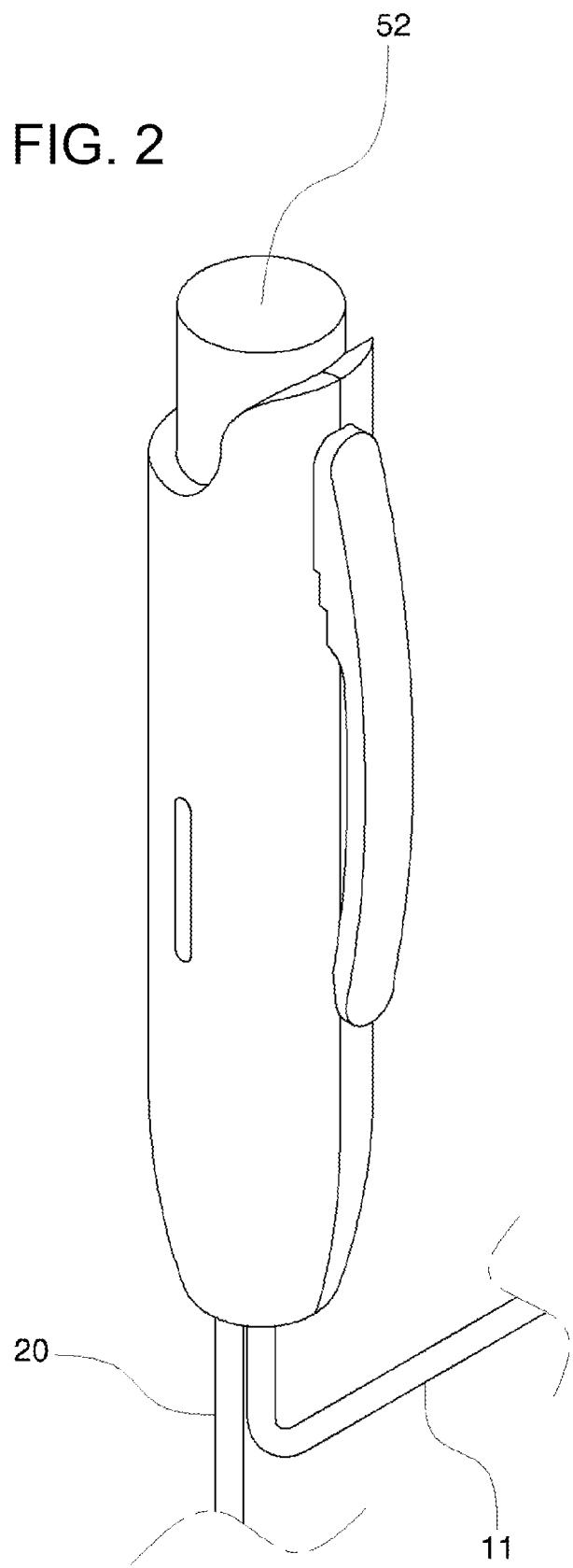
FIG. 2 is a perspective view illustrating the liquid injector according to an embodiment of the present disclosure.
Figure 3:
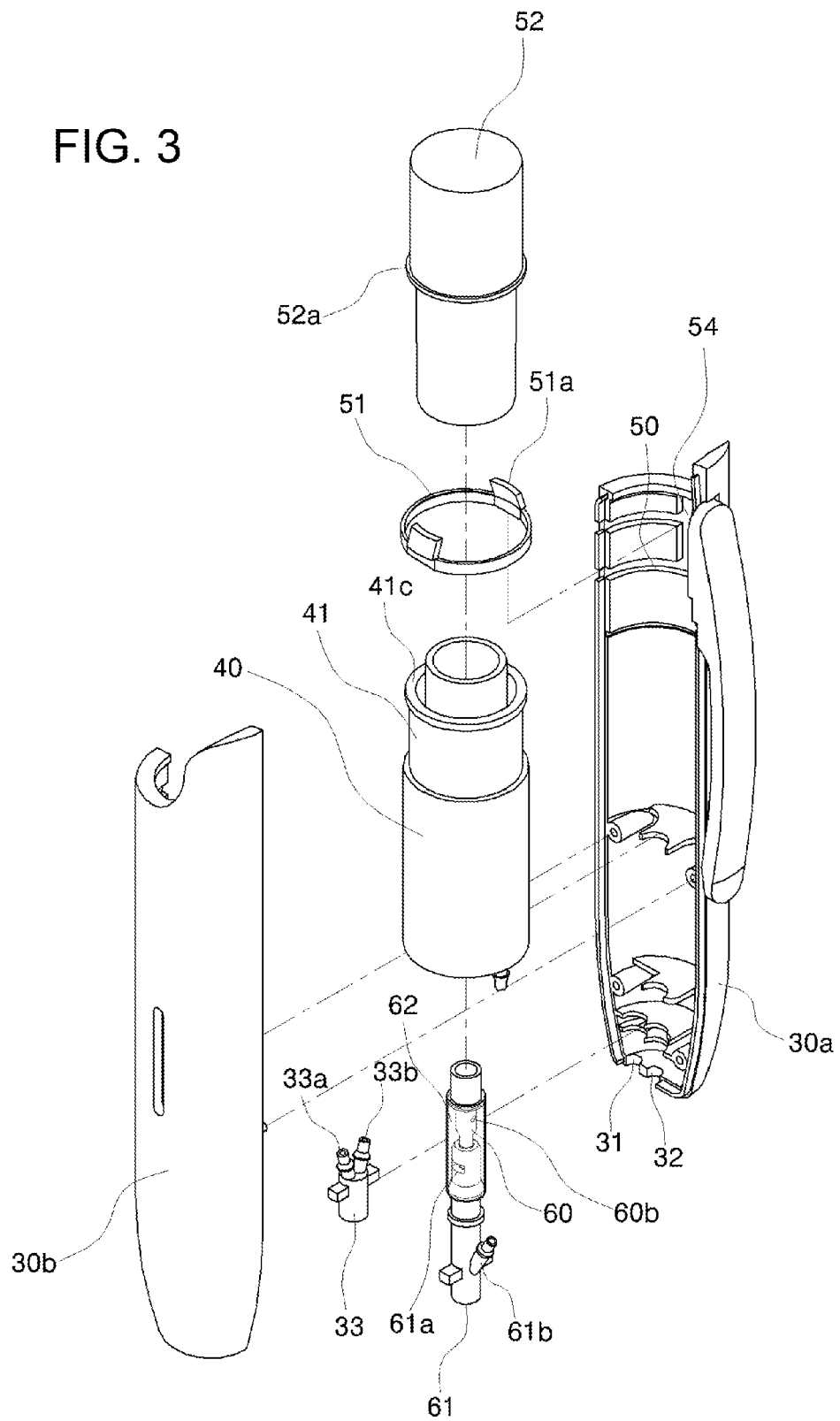
FIG. 3 is an exploded perspective view illustrating the liquid injector according to an embodiment of the present disclosure.

FIG. 1 illustrates a connection state of a liquid injector, a liquid supply, and an injection hose 20 according to an embodiment of the present disclosure. FIG. 2 is a perspective view illustrating the liquid injector according to an embodiment of the present disclosure. FIG. 3 is an exploded perspective view illustrating the liquid injector according to an embodiment of the present disclosure.

Referring to FIGS. 1 to 3, as illustrated, the present disclosure includes a liquid supply 10 that accommodates a liquid, an injection hose 20 that injects the liquid sent from the liquid supply 10 into the body of the patient, and a liquid injector 30 that partially catches and charges the liquid that is being sent to the injection hose 20 at an intermediate point when the liquid supply 10 supplies the liquid to the injection hose 20. As illustrated in FIG. 1, the liquid supply 10 supplies liquid to the liquid injector 30 via a hose 11.

Then, the liquid injector 30 extends from one side to another side, and a pair of cases 30a and 30b are assembled such that an inlet port 31 connected to a hose of the liquid supply 10, together with an outlet port 32 connected to the injector hose 20 are formed at one side thereof and a push button 52 is installed at an opposite end thereof so that if the push button 52 is pushed, the liquid charged in the liquid injector 30 is further supplied to the patient in addition to the liquid that is being normally supplied by the liquid supply 10.

Then, the liquid injector 30 includes a fixed quantity charging unit 43 that charges a fixed quantity of liquid, a brake button unit 53 that discharges the liquid charged in the fixed quantity charging unit 43, and a continuous injection unit 64 that continuously sends the liquid to the injector hose 20 little by little while accommodating the liquid discharged by the brake button unit 53 so that the liquid is discharged only when a fixed quantity of liquid is charged in the fixed quantity charging unit 43 and then the discharged liquid is continuously injected into the body of the patient little by little.

Figure 4:
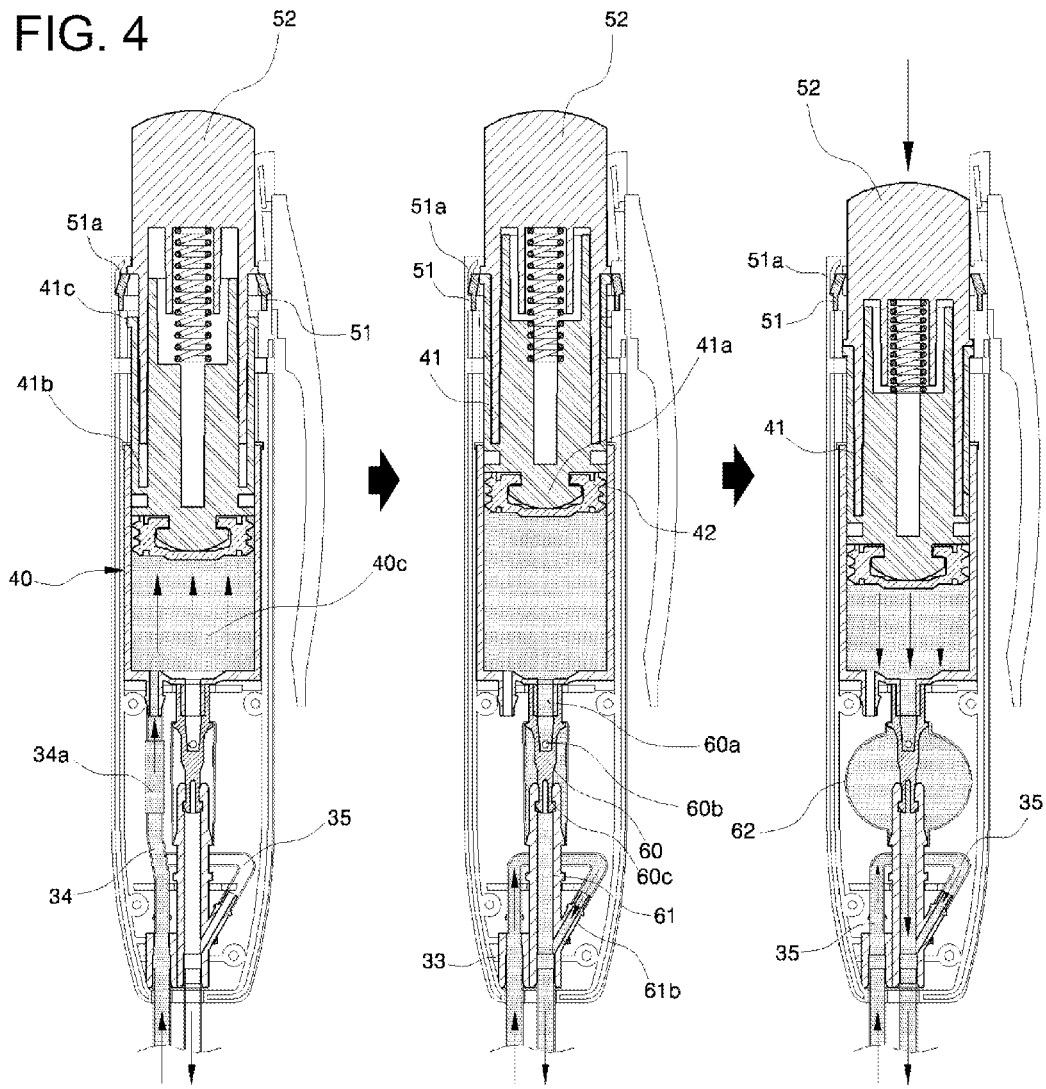
FIG. 4 is a view illustrating an operational state of the liquid injector according to an embodiment of the present disclosure.

FIG. 4 illustrates a process of charging and discharging liquid to and from the liquid injector according to an embodiment of the present disclosure.

Referring to FIG. 4, a Y-shaped branch pipe 33 and a connection pipe 61 are installed in the inlet port 31 and the outlet port 32 formed at a tip end of the case, one side pipe 33a of the branch pipe 33 is connected to a charge hole 40a (or an inlet) of a cylinder 40 by a connection hose 34, and a check filter 34a is installed between the charge hole 40a and the branch pipe 33 such that the liquid flows only in one direction. Thus, the check filter 34a acts as a one-way valve.

The connection pipe 61 of the inlet port 31 is connected to a connector 60 of the cylinder 40 by using a resilient tube 62 and a protruding pipe 61b of the connection pipe 61 is connected to an opposite side pipe 33b of the branch pipe 33 with another connection hose 35 so that if the liquid is normally introduced inwards through the inlet port 31 such that a fixed quantity of liquid is charged in the cylinder 40, the entire quantity of liquid introduced through the inlet port 31 flows to the connection pipe 61 through the branch pipe 33 and is introduced into the body of the patient.

If the liquid is not charged in the cylinder 40, a partial or entire quantity of the liquid introduced through the inlet port 31 flows to the cylinder 40 and is charged in an inner accommodation space 40c. Then, the piston 41 starts to be lifted by the liquid introduced into the cylinder 40. Moreover, if the piston 41 is lifted to a predetermined height, a fixed quantity of liquid is charged.

Figure 5:
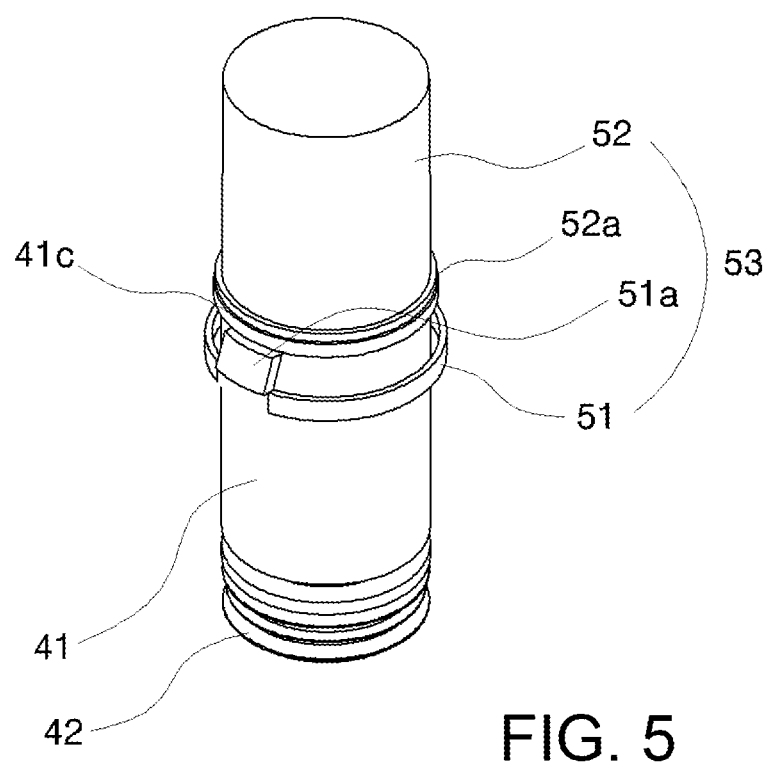
FIG. 5 is a perspective view illustrating a brake button unit of the liquid injector according to an embodiment of the present disclosure.
Figure 6:
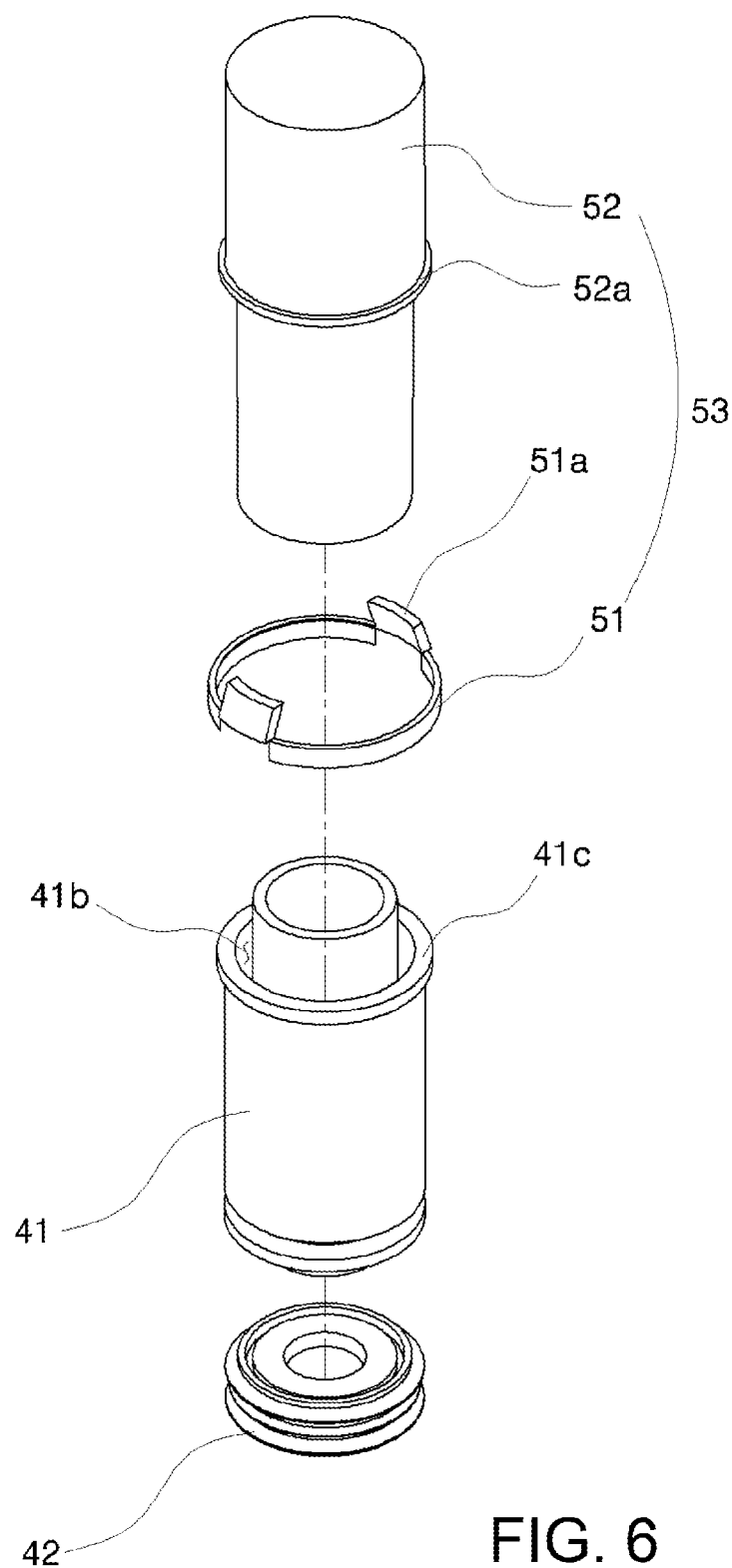
FIG. 6 is an exploded perspective view illustrating the brake button unit of the liquid injector according to an embodiment of the present disclosure.
Figure 7:
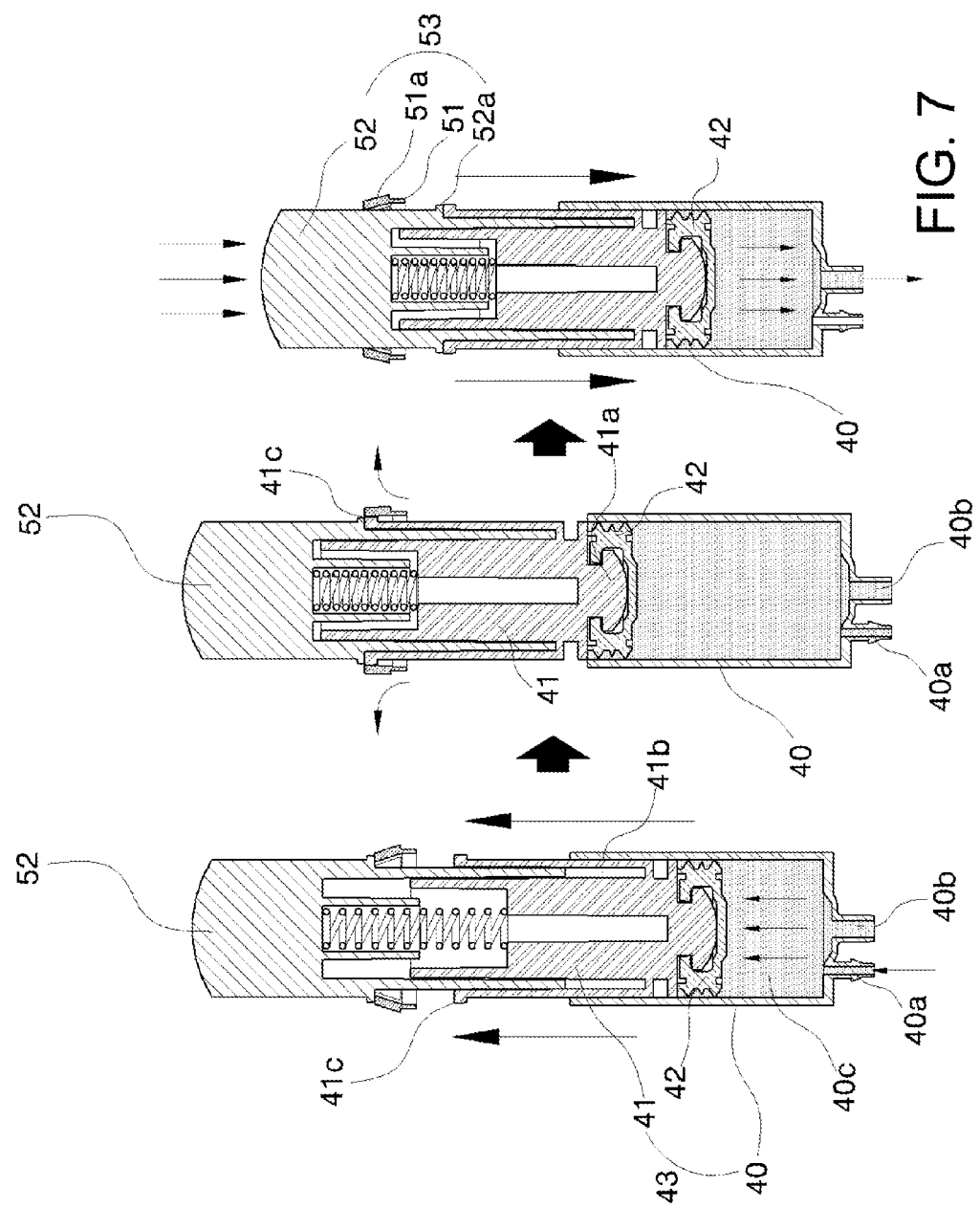
FIG. 7 is a view illustrating an operational state of the brake button unit of the liquid injector according to an embodiment of the present disclosure.

FIG. 5 is a perspective view illustrating the brake button unit and the piston according to an embodiment of the present disclosure. FIG. 6 is an exploded perspective view of FIG. 5 according to an embodiment of the present disclosure. FIG. 7 is a flowchart illustrating an operation of the piston and the brake button unit according to an embodiment of the present disclosure.

Referring to FIGS. 5 to 7, the fixed quantity charging unit 43 charges a fixed quantity of liquid in the interior of the cylinder 40 when the piston 41 is lifted to a lower end of the push button 52 installed at an upper end of the case, is raised to a predetermined height while being adhered to the lower end of the push button 52, and is stopped.

Then, if the push button 52 adhered to the piston 41 is pushed, the fixed quantity of liquid charged in the interior of the cylinder 40 is discharged.

For reference, a boss 41a is formed at a lower end of the piston 41, a packing 42 is mounted on the boss 41a and is adhered to an inner wall of the cylinder 40, an insertion space 41b is formed at an upper portion of the piston 41, and a lower end of the push button 52 is inserted into the insertion space 41b. Then, a protruding step 41c is formed at an upper periphery of the piston 41.

A stop groove 50 is formed in the cases 30a and 30b in which the piston 41 and the cylinder 40 are installed, and an annular stop rim 51 having a ring shape is positioned in the stop groove 50.

A pair of stop pieces 51a protrude from an upper portion of the stop rim 51 to be inclined inwards, and the piston 41 is inserted into the stop rim 51.

Accordingly, if the piston 41 is lifted by the liquid charged in the interior of the cylinder 40, the protruding step 41c of the piston 41 pushes out the stop pieces 51a of the stop rim 51 located on the outer side so that the stop pieces 51a are opened while being resiliently supported.

The push button 52 having a support step 52a at a lower end thereof is installed at an upper portion of the piston 41, a lower portion of the push button 52 is inserted into the insertion space 41b of the piston 41, and the support step 52a formed at an outer side of the push button 52 is supported by the stop piece 51a and is stopped. Then, a resilient body is inserted into the insertion space 41b to return the push button 52 lowered downwards to an original state.

Accordingly, when the fixed quantity charging unit 43 is fully filled with the liquid and the piston 41 is adhered to the push button 52, the protruding step 41c formed on the outer side of the piston 41 resiliently supports and opens the stop pieces 51a and is adhered to the support step of the push button 52.

Accordingly, when a predetermined quantity of liquid is not charged in the fixed quantity charging unit 43, the support step 52a of the push button 52 is supported by the stop pieces 51a and the downward movement of the push button is restricted, but if a predetermined quantity of liquid is charged in the fixed quantity charging unit 43 such that the protruding step 41c of the piston 41 resiliently supports and opens the stop pieces 51a, the protruding step 41c and the support step 52a of the push button 52 are adhered to each other. Then, because the stop pieces are opened if the push button is pushed, the support step and the protruding step are lowered along a guide rod 54 while being adhered to each other so that the fixed quantity of liquid accommodated in the interior of the cylinder is discharged.

For reference, according to the embodiment of the present disclosure, the stop rim 51 may be widened or closed while being easily resiliently supported by the piston by cutting away a lower portion of the stop pieces 51a.

If a fixed quantity of liquid charged by the fixed quantity charging unit 43 and the brake button unit 53 is discharged, the liquid is sent to the outside of the cylinder 40 though a discharge hole 40b (or an outlet).

Figure 8:
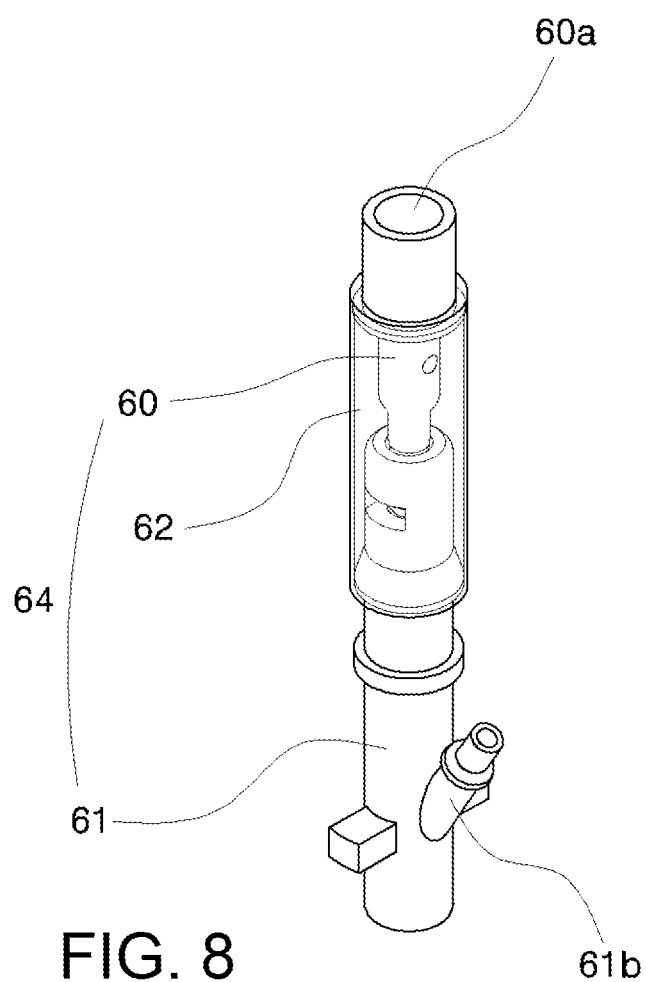
FIG. 8 is a perspective view illustrating a continuous injection unit of the liquid injector according to an embodiment of the present disclosure.
Figure 9:
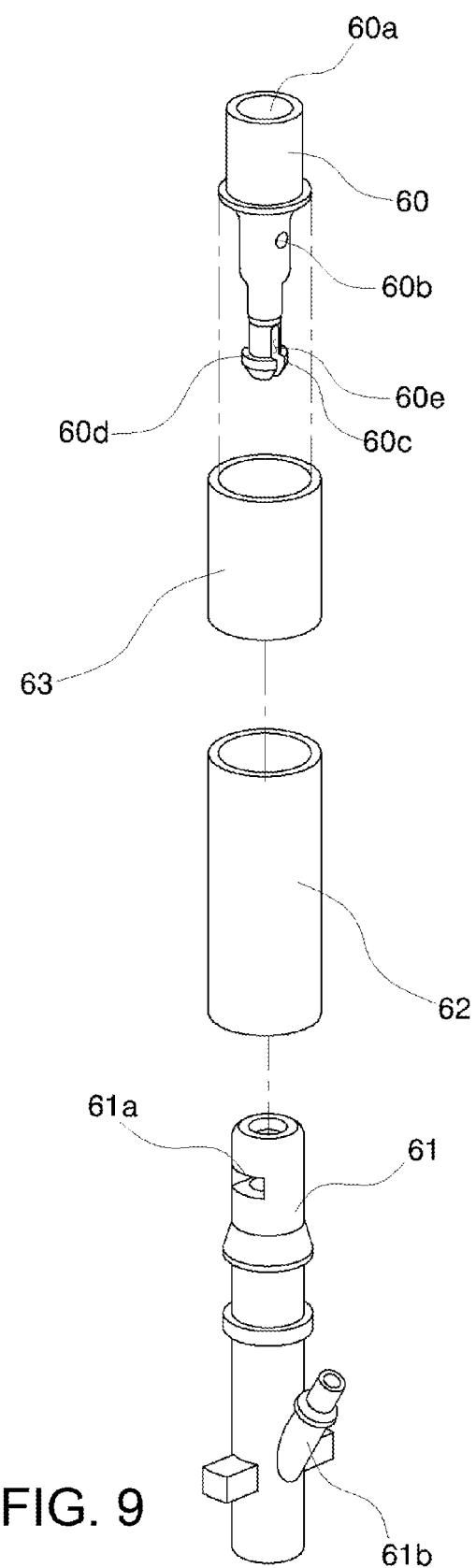
FIG. 9 is an exploded perspective view illustrating the continuous injection unit of the liquid injector according to an embodiment of the present disclosure.
Figure 10:
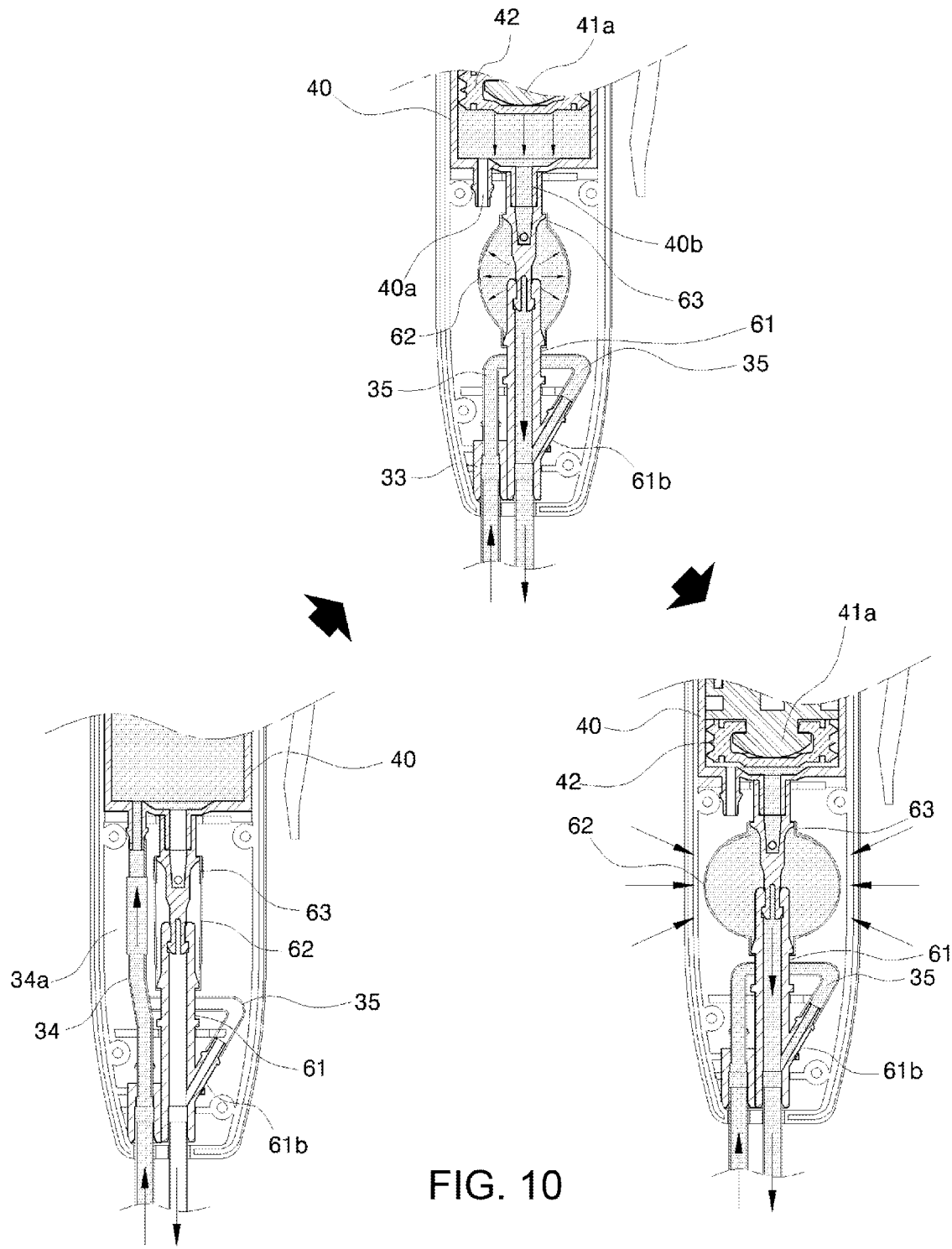
FIG. 10 is a view illustrating an operational state of the continuous injection unit of the liquid injector according to an embodiment of the present disclosure.

FIG. 8 illustrates the continuous injection unit 64 mounted between the discharge hole 40b and the outlet port 32 according to an embodiment of the present disclosure. FIG. 9 illustrates a disassembled state of the continuous injection unit 64 according to an embodiment of the present disclosure. FIG. 10 is a flowchart illustrating an operation of the continuous injection unit according to an embodiment of the present disclosure.

Referring to FIGS. 8 to 10, the continuous injection unit 64 accommodates a fixed quantity of liquid while a resilient tube 62 is expanded.

Then, the liquid absorbed in the resilient tube 62 is continuously sent to the outside of the outlet port 32 by a contraction force of the resilient tube 62 that returns the resilient tuber 62 to an original state and is injected into the body of the patient.

Then, one side of the connector 60 is inserted into the discharge hole 40b of the cylinder 40 and is fixed, an opposite side of the connector 60 is inserted into the connection pipe 61 and is fixed, an inward recess 60a is formed at one side of the connector 60, and an injection hole that laterally passes through the inward recess 60a is formed in the inward recess 60a. One end of the resilient tube 62 is fixed to the upper side of the injection hole.

Accordingly, the fixed quantity of liquid discharged to the outside of the discharge hole 40b of the cylinder 40 is accommodated in the interior of the resilient tube 62 through an inward hole 60b of the connector 60, and then the resilient tube 62 absorbs the fixed quantity of liquid discharged to the outside of the cylinder 40 while being expanded.

Then, an opposite end of the connector 60 is cut away longitudinally with respect to the center thereof to form a pair of coupling pieces 60c and coupling steps 60d are formed at ends of the coupling pieces 60c so that when the coupling pieces 60c are inserted into the connection pipe 61, the coupling steps 60d are located inside coupling recesses 61a of the connection pipe 61 and are stopped.

Accordingly, because the resilient tube 62 mounted on the outside is expanded and contracted only in one direction with respect to the coupling pieces if the connector 60 and the connection pipe 61 are connected to each other, the liquid is accommodated in the resilient tube while the resilient tube is neither deflected nor bent as the restoring force of the resilient tube is maximized. Furthermore, as the liquid accommodated in the resilient tube 62 is introduced into the connection pipe 61 through a cutaway portion 60e between the coupling pieces 60c by a restoring force of the resilient tube 62, the fixed quantity of liquid is continuously sent to the outside of the outlet port 32 little by little.

Then, the resilient tube 62 may accommodate liquid, a quantity of which is larger than the quantity of the liquid charged in the cylinder 40, but only one dose of liquid is accommodated by making the space, in which the resilient tube 62 is expanded, the same as the area of the cylinder 40.

Moreover, according to the embodiment of the present disclosure, a fixed tube 63 that is resilient may be installed inside the resilient tube 62. That is, the fixed tube 63 is installed while surrounding the injection hole of the connector 60 and the resilient tube 62 is fixedly installed on the fixed tube 63 so that if the liquid accommodated in the interior of the cylinder 40 is discharged, the liquid pushed to the outside of the injection hole is accommodated inside the resilient tube 62. Furthermore, if no liquid is pushed to the outside of the injection hole, the fixed tube is contracted to block the injection hole.

Furthermore, when the expanded resilient tube 62 pushes out the liquid, the fixed tube 63 prevents the liquid from returning into the injection hole so that only the resilient tube located at an intermediate point absorbs the liquid and then sends the liquid to the outside.

According to the present disclosure, one dose of liquid is discharged only when the charging is completed if the push button is pushed, and then the discharged liquid is absorbed in the resilient tube 62 and then a small quantity of liquid is continuously sent to the body of the patient by a returning force to be safely used.

While the present disclosure has been shown and described with reference to various embodiments thereof, it will be understood by those skilled in the art that various changes in form and details may be made therein without departing from the spirit and scope of the present disclosure as defined by the appended claims and their equivalents.

What is claimed is:

1. A liquid injector that additionally supplies charged liquid while continuously injecting a small quantity of liquid, the liquid injector comprising:
   a fixed quantity charging device that is adhered to a lower end of a push button when a piston is lifted by liquid introduced into an interior of a cylinder and then is stopped to charge a fixed quantity of liquid in the interior of the cylinder, the cylinder comprising a charge hole and a discharge hole;
a one-way valve in communication with the charge hole such that liquid flows into the cylinder through the charge hole;
a brake button device that, if the lifted piston and the push button are adhered to each other while a downward movement of the push button is stopped, lowers the push button together with the piston downwards as the stopped downward movement of the push button is released;
a continuous injection device that, by a restoring force of a resilient tube that is expanded while accommodating a fixed quantity of liquid discharged to outside of the cylinder, through the discharge hole, by the brake button device, continuously pushes out the liquid accommodated in the interior of the resilient tube; and
a pair of coupling pieces that are cut away longitudinally and face each other, the pair of coupling pieces being formed on an opposite side of the connector and coupling steps being formed at ends of the pair of coupling pieces,
wherein the pair of coupling pieces are inserted into the connection pipe to be stopped and fixed by a coupling recess so that the liquid accommodated in the interior of the resilient tube is injected into the body of the patient while being discharged to outside of the connection pipe through a cutaway portion between the pair of coupling pieces when the resilient tube is contracted and expanded with respect to the pair of coupling pieces,
wherein the continuous injection device comprises:
    a connector that has an inward recess, one side of which is mounted on the discharge hole of the cylinder and an inward hole that passes through the inward recess laterally,
    a connection pipe mounted on an outlet port of a plurality of cases, and
    a resilient tube fixedly installed between the connector and the connection pipe,
wherein the fixed quantity of liquid discharged to outside of the discharge hole of the cylinder is accommodated in the interior of the resilient tube through the inward hole, and
wherein a small quantity of liquid is continuously sent to outside of the connection pipe by a force by which the resilient tube is contracted while accommodating the fixed quantity of liquid discharged to outside of the cylinder is contracted.

2. The liquid injector of claim 1, further comprising:
a fixed tube, the fixed tube is installed inside the resilient tube,
wherein the fixed tube is fixedly installed while surrounding the inward hole of the connector so that the liquid discharged to outside of the inward hole is discharged to outside of the fixed tube and is accommodated only in the interior of the resilient tube.

3. A liquid injector that additionally supplies charged liquid while continuously injecting a small quantity of liquid, the liquid injector comprising:
a fixed quantity charging device configured to connect to a lower end of a push button when a piston is lifted by liquid introduced into an interior of a cylinder and then is stopped to charge a fixed quantity of liquid in the interior of the cylinder;

a brake button device that, if the lifted piston and the push button are adhered to each other while a downward movement of the push button is stopped, the brake button device lowers the push button together with the piston downwards as the stopped downward movement of the push button is released; and
a continuous injection device that, by a restoring force of a resilient tube that is expanded while accommodating a fixed quantity of liquid discharged to outside of the cylinder by the brake button device, the continuous injection device continuously pushes out the liquid accommodated in the interior of the resilient tube,
wherein the fixed quantity charging device comprises:
    the cylinder, the cylinder comprises a charge hole and a discharge hole at one side thereof and an accommodation space at an opposite side thereof,
    the piston, a lower end of the piston is inserted into the accommodation space of the cylinder, the accommodation space comprises an insertion space at an end thereof and a protruding step at a periphery thereof,
    a resilient body that is inserted into the insertion space of the piston; and
    a push button that has a support step at a periphery thereof above the resilient body, and
wherein the protruding step and the support step of the push button are adhered to each other when the piston is lifted by the liquid introduced into the interior of the cylinder, and then is stopped at a predetermined location to charge a fixed quantity of liquid in the interior of the cylinder.

4. The liquid injector of claim 3,
wherein the brake button device comprises:
    a ring-shaped stop rim that has inward stop pieces, and
    a plurality of cases each comprising:
        a stop groove in which the ring-shaped stop rim is positioned, and
        a guide rod,
wherein the piston is mounted on the inside of the plurality of cases while being inserted into the ring-shaped stop rim, and
wherein, if the piston is lifted, the support step of the push button mounted on the inward stop pieces and the protruding step of the piston are adhered to each other while the inward stop pieces of the ring-shaped stop rim are widened outwards by the protruding step so that the push button and the piston, which are adhered to each other, are pushed downwards to discharge the fixed quantity of liquid to outside of the cylinder only when the fixed quantity of liquid is charged in the cylinder.

5. The liquid injector of claim 4,
wherein the inward stop pieces comprise lower ends, and
wherein the lower ends are cutaway such that the inward stop pieces located on the upper side are resiliently supported by the ring-shaped stop rim.

6. A liquid injector that additionally supplies charged liquid while continuously injecting a small quantity of liquid, the liquid injector comprising:
a fixed quantity charging device that is adhered to a lower end of a push button when a piston is lifted by liquid introduced into an interior of a cylinder and then is stopped to charge a fixed quantity of liquid in the interior of the cylinder, the cylinder comprising a charge hole and a discharge hole;
a one-way valve in communication with the charge hole such that liquid flows into the cylinder through the charge hole;

a brake button device that, if the lifted piston and the push button are adhered to each other while a downward movement of the push button is stopped, lowers the push button together with the piston downwards as the stopped downward movement of the push button is released;

a continuous injection device that, by a restoring force of a resilient tube that is expanded while accommodating a fixed quantity of liquid discharged to outside of the cylinder, through the discharge hole, by the brake button device, continuously pushes out the liquid accommodated in the interior of the resilient tube; and a fixed tube is installed inside the resilient tube, wherein the continuous injection device comprises:

a connector that has an inward recess, one side of which is mounted on the discharge hole of the cylinder and an inward hole that passes through the inward recess laterally, a connection pipe mounted on an outlet port of a plurality of cases, and a resilient tube fixedly installed between the connector and the connection pipe, wherein the fixed quantity of liquid discharged to outside of the discharge hole of the cylinder is accommodated in the interior of the resilient tube through the inward hole, wherein a small quantity of liquid is continuously sent to outside of the connection pipe by a force by which the resilient tube is contracted while accommodating the fixed quantity of liquid discharged to outside of the cylinder is contracted, and wherein the fixed tube is fixedly installed while surrounding the inward hole of the connector so that the liquid discharged to outside of the inward hole is discharged to outside of the fixed tube and is accommodated only in the interior of the resilient tube.

* * * * *